United States Patent [19]

Relenyi et al.

[11] Patent Number: 5,025,038

[45] Date of Patent: Jun. 18, 1991

[54] PROCESS FOR THE PREPARATION OF ANTIMICROBIAL FORMULATIONS OF 2-(ALKYLTHIO)ETHANAMINE HYDROHALIDES

[75] Inventors: Attila G. Relenyi; Charles D. Gartner, both of Midland, Mich.

[73] Assignee: The Dow Chemical Company, Midland, Mich.

[21] Appl. No.: 596,431

[22] Filed: Oct. 12, 1990

Related U.S. Application Data

[62] Division of Ser. No. 318,787, Mar. 3, 1989, Pat. No. 4,982,004.

[51] Int. Cl.$^5$ .................... A01N 33/08; A01N 37/18
[52] U.S. Cl. .................................. 514/665; 514/629
[58] Field of Search .......................... 514/665, 629

[56] References Cited

U.S. PATENT DOCUMENTS

| | | | |
|---|---|---|---|
| 3,291,683 | 12/1966 | Lamb | 514/665 |
| 3,414,620 | 12/1968 | Bresson et al. | 564/340 |
| 4,086,273 | 4/1978 | Berazosky et al. | 564/215 |
| 4,086,274 | 4/1978 | Kaiser et al. | 564/488 |
| 4,251,459 | 2/1981 | Bargeron et al. | 564/215 |
| 4,621,086 | 11/1986 | Capps | 514/287 |
| 4,816,061 | 3/1989 | Walter, Jr. et al. | 514/665 |

OTHER PUBLICATIONS

C.A. 71 53576q., 1969, Kalopissis et al.

*Primary Examiner*—Allen J. Robinson

[57] ABSTRACT

A method for preparing antimicrobial formulations of 2-(alkylthio)ethanamines hydrohalides is disclosed. The formulations are prepared directly from the hydrolysis product of 2-(alkylthio)ethyl propionamides, thereby eliminating both waste streams and isolation procedures.

2 Claims, No Drawings

PROCESS FOR THE PREPARATION OF ANTIMICROBIAL FORMULATIONS OF 2-(ALKYLTHIO)ETHANAMINE HYDROHALIDES

CROSS-REFERENCE TO RELATED APPLICATION

This is a divisional of application Ser. No. 318,787, filed Mar. 3, 1989, now U.S. Pat. No. 4,982,004.

FIELD OF THE INVENTION

The present invention is directed to a process for preparing antimicrobial formulations of 2-(alkylthio)ethanamine hydrohalides. More particularly, the present invention is directed to a process for preparing such formulations directly from the reaction mixture resulting from the hydrolysis of the corresponding 2-(alkylthio)ethyl propionamides.

BACKGROUND OF THE INVENTION 2-(Alkylthio)ethanamines in which the alkylthio group contains 8 to 12 carbon atoms are known to possess antimicrobial properties: see, for example, U.S. Pat. No. 3,291,683 and European Patent Application Publication No. 266,828. A process for the preparation of 2-(alkylthio)ethanamines from alkyl mercaptans and 2-oxazolines in the presence of a Lewis acid catalyst is taught in U.S. Pat. No. 4,086,273. In that process, for example, 2-ethyl-2-oxazoline (I) and the alkyl mercaptan (II) react in the presence of a Lewis acid catalyst to form a 2-(alkylthio)ethyl propionamide (III) which is subsequently hydrolyzed with an aqueous hydrohalic acid to the 2-(alkylthio)ethanamine hydrohalide (IV) and propionic acid.

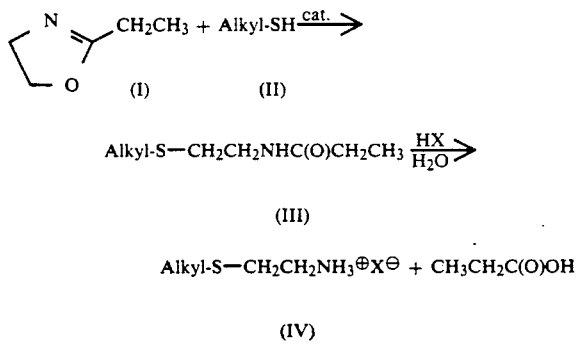

The resulting solution is very acidic and is therefore corrosive to metals and human tissue. Furthermore, since the 2-(alkylthio)ethanamine hydrohalide (IV) is a quaternary amine, it is not surprising that the product behaves as a surfactant. As a result, neutralization of the reaction mixture often leads to emulsions. Formulations of such materials are often unstable with respect to phase separation, particularly when subjected to one or more freeze-thaw cycles. It would be desirable to have a stable antimicrobial formulation of 2-(alkylthio)ethanamine hydrohalides that is non-corrosive and non-settling. Moreover, it would be highly desirable to be able to form such an antimicrobial formulation directly from the reaction mixture that results from the hydrolysis of the 2-(alkylthio)ethyl propionamide (III) without any undue unit operations or waste streams.

SUMMARY OF THE INVENTION

The present invention is directed to a process for preparing antimicrobial formulations which contain as the active ingredient a 2-(alkylthio)ethanamine hydrohalide of the formula

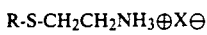

wherein
R represents a straight or branched chain alkyl group of 8 to 12 carbon atoms, and
$X^{\ominus}$ represents a chloride or bromide anion which comprises:
(a) hydrolyzing an amide of the formula

wherein
R is as previously defined, to the 2-(alkylthio)ethanamine hydrohalide and propionic acid by contacting the amide with aqueous hydrochloric or hydrobromic acid:
(b) neutralizing any remaining hydrochloric or hydrobromic acid and a part of the propionic acid formed by contacting the amide hydrolysate with aqueous potassium hydroxide: and
(c) diluting the neutralized hydrolysate with propylene glycol and, optionally, additional water.

In another aspect of the present invention, the amide to be hydrolyzed is prepared by contacting in the liquid phase an appropriate aliphatic mercaptan with 2-ethyl-2-oxazoline in the presence of a Lewis acid catalyst. Optionally, the above steps may all be conducted in a single reaction vessel.

The formulations produced by the present process provide still another embodiment of the invention.

DETAILED DESCRIPTION OF THE INVENTION

The 2-(alkylthio)ethyl propionamides which are employed as the starting materials in the process of the present invention are known compounds. Preferably, they are prepared from the appropriate alkyl mercaptan and 2-ethyl-2-oxazoline as described in U.S. Pat. No. 4,086,273 which is incorporated by reference herein. When the 2-(alkylthio)ethyl propionamides are prepared in this way, the initial step involves the reaction of 2-ethyl-2-oxazoline with an aliphatic mercaptan in the presence of a Lewis acid catalyst. Preferably, the catalyst is zinc chloride and the reaction is conducted in the absence of solvent. The reaction is normally carried out under a nitrogen atmosphere because air has been found to be slightly detrimental in terms of product color and impurity formation.

In a typical procedure the mercaptan is vacuum loaded into the reaction vessel at room temperature. The catalyst is added and a slight vacuum is drawn to remove oxygen. The vacuum is broken with nitrogen and the mixture is stirred and heated to between about 110° C. and about 150° C. before the addition of the ethyloxazoline is begun. About a one to two percent molar excess of ethyloxazoline with respect to the mercaptan is usually employed. The ethyloxazoline is added at a rate to help control the temperature of the exothermic reaction. Generally, the temperature is controlled between 135° C. and 225° C. Catalyst level is not very critical, and additional catalyst may be added during the addition of the ethyloxazoline if necessary. Generally, about 3000 parts per million by weight of catalyst is employed.

After completion of the reaction, generally within one hour after the addition of the ethyl-oxazoline, the reactor is cooled to about 100° C. and the pressure is adjusted to atmospheric. Concentrated hydrochloric or hydrobromic acid is added and the hydrolysis is conducted at an elevated temperature.

The hydrolysis reaction is preferably conducted with concentrated hydrochloric acid. At least one mole of HCl per mole of propionamide is required. Preferably, a 1 to 5 percent molar excess of HCl is employed.

The hydrolysis is typically run at a temperature from about 100° C. to about 175° C. Above about 100° C., the reaction must be run in a sealed reactor, in which case the vapor pressure of the reaction mixture can range from about 15 to about 130 pounds per square inch absolute (psia). The hydrolysis is usually completed in about 1 to 12 hours.

The neutralization of the excess hydrochloric or hydrobromic acid and a fraction of the by-product propionic acid is conducted using potassium hydroxide. Potassium hydroxide has unexpectedly been found to be advantageously employed for reducing emulsions frequently encountered with other bases. The neutralization is preferably performed above approximately 70° C. so as to avoid mixing difficulties associated with higher viscosity at lower temperatures. From about 0.2 to about 0.6 equivalents of KOH per equivalent of hydrochloric or hydrobromic acid are generally employed. The potassium hydroxide is preferably added as an aqueous solution containing from about 5 to about 50 weight percent KOH.

After the neutralization is complete, formulations are directly prepared by addition of the appropriate amounts of propylene glycol and water to the reaction mixture. In practice, it is often more convenient to transfer the neutralized reaction mixture into a larger vessel already containing the calculated amounts of propylene glycol and water. Prior to the preparation of the formulation, the neutralized reaction mixture may be analyzed by conventional techniques such as, for example, liquid chromatography, in order to determine the precise amount of the active ingredient present and to calculate the amounts of propylene glycol and water necessary for producing the desired formulation. Because of the nearly quantitative reaction yields, however, the amounts of propylene glycol and water to be added can conveniently be calculated on the basis of the raw materials charged.

Propylene glycol has been found to be uniquely suited to stabilize formulations prepared directly from the neutralized reaction mixture. Such formulations remain free of phase separation and precipitation despite undergoing freeze-thaw transitions.

By practicing the process of this invention, formulations comprising the following compositions can be prepared:

|  | Weight Percent |
| --- | --- |
| 2-(alkylthio)ethanamine hydrohalide | 1–40 |
| propylene glycol | 1–50 |
| water | 30–95 |
| propionic acid | 0.25–10 |
| potassium propionate | 0–10 |

Formulations of the following compositions are preferred:

|  | Weight Percent |
| --- | --- |
| 2-(alkylthio)ethanamine hydrohalide | 5–35 |
| propylene glycol | 5–35 |
| water | 40–65 |
| propionic acid | 1–8 |
| potassium propionate | 0–3 |

Optionally, surfactants or antifoam agents can be added to the formulations.

The following examples illustrate the present invention and the manner in which it can be practiced, but as such are not to be construed as limitations upon the overall scope thereof.

EXAMPLE I 2-(Decylthio)ethanamine Hydrochloride Formulation

A) Preparation of Decylthioethyl propionamide

Approximately 225 pounds (lbs) of decyl mercaptan were vacuum loaded at room temperature into a 100 gallon (gal) glass-lined Pfaudler reactor equipped with an agitator and jacketed with a heat transfer fluid. Vacuum was drawn on the reactor prior to loading and the reactor was sealed to minimize loss of mercaptan. Zinc chloride (1.25 lbs; 3,500 ppm) was added through the manhole. A slight vacuum was drawn and then broken with nitrogen to remove any oxygen which may have entered the system during the catalyst addition.

The system was heated to approximately 140° C. before addition of the ethyloxazoline began. The 2-ethyl-2-oxazoline (130 lbs) was added in about 45 minutes (3 lbs/min). After addition of the ethyloxazoline, 30 min were allowed for the completion of the reaction. In general, a reduction in reactor pressure signals the completion of the reaction.

The reactor was cooled to about 120° C. and brought to atmospheric pressure so that the reactor could be sampled through the manhole. The decylthioethyl propionamide quickly solidifies at room temperature.

B) Hydrolysis

After cooling the reactor to 120° C., 155 lbs of 32 weight percent hydrochloric acid was added to the reaction mixture. The reactor was heated to 150–160° C., where the vapor pressure of the system was approximately 60 psia. The temperature was maintained near 150° C. for 2 hours (hr) to complete the hydrolysis.

C) Neutralization

After the hydrolysis is complete, the reactor is cooled to about 100° C. and slowly vented through a caustic scrubber. The 0.2 equivalents of KOH (60 lbs of 25 weight percent solution), based upon the HCl added, was introduced in under 1 min.

D) Formulation

A 1000 gal glass-lined Pfaudler reactor, equipped with an agitator and jacketed with tempered water, was charged with 300 lbs of propylene glycol and 1200 lbs of water. The neutralized reaction mixture was transferred from the 100 gal reactor to the propylene glycol/water solution. Antifoam agent (3 lbs) was optionally added. The resulting formulation had the following composition:

| | |
|---|---|
| 2-(n-decylthio)ethanamine hydrochloride | 15.5 WT percent |
| propylene glycol | 14.5 WT percent |
| water | 64.4 WT percent |
| propionic acid | 3.9 WT percent |
| potassium propionate | 1.1 WT percent |
| miscellaneous | 0.6 WT percent |

What is claimed is:

1. An antimicrobial composition which comprises 1 to 40 weight percent of a 2-(alkylthio)ethanamine hydrohalide of the formula R-SCH$_2$CH$_2$NH$_3$⊕X⊖, wherein R represents a straight or branches chain alkyl group of 8 to 12 carbon atoms and X⊖ represents a chloride or bromide anion, 1 to 50 weight percent propylene glycol, 30 to 95 weight percent water, 0.25 to 10 weight percent propionic acid, and 0 to 10 weight percent potassium propionate, wherein the antimicrobial composition is prepared by a process which comprises the steps of:

(a) hydrolyzing an amide of the formula

R-S-CH$_2$CH$_2$-NH-C(O)-CH$_2$CH$_3$ wherein
R is as previously defined,
to the 2-(alkylthio)ethanamine hydrohalide and propionic acid by contacting the amide with aqueous hydrochloric or hydrobromic acid;

(b) neutralizing any remaining hydrochloric or hydrobromic acid and a part of the propionic acid formed by contacting the amide hydrolysate with aqueous potassium hydroxide; and (c) diluting the neutralized hydrolysate with propylene glycol and, optionally, additional water.

2. The antimicrobial composition of claim 1 which comprises 5 to 35 weight percent 2-(alkylthio)ethanamine hydrochloride, 5 to 35 weight percent propylene glycol, 40 to 65 weight percent water, 1 to 8 weight percent propionic acid, and 0 to 3 weight percent potassium propionate.

* * * * *